United States Patent [19]

Dimitri

[11] 3,992,532

[45] Nov. 16, 1976

[54] FLOWABLE PESTICIDE FORMULATIONS

[75] Inventor: Mitchell S. Dimitri, Charleston, S.C.

[73] Assignee: Westvaco Corporation, New York, N.Y.

[22] Filed: Jan. 2, 1975

[21] Appl. No.: 538,002

Related U.S. Application Data

[63] Continuation-in-part of Ser. No. 404,045, Oct. 5, 1973, abandoned, which is a continuation of Ser. No. 181,243, Sept. 16, 1971, abandoned.

[52] U.S. Cl. .............................. 424/213; 424/300; 424/352; 424/365
[51] Int. Cl.² ...................... A01N 9/36; A01N 9/30; A01N 9/32; A01N 9/12
[58] Field of Search .......... 424/213, 352, 364, 365, 424/300

[56] References Cited

UNITED STATES PATENTS

| | | | |
|---|---|---|---|
| 2,834,731 | 5/1958 | Carpenter | 424/358 |
| 2,858,250 | 10/1958 | Geary | 424/358 |
| 2,871,155 | 1/1959 | Klomparens et al. | 424/358 |
| 2,957,803 | 10/1969 | Woods | 424/168 |

FOREIGN PATENTS OR APPLICATIONS

| | | | |
|---|---|---|---|
| 815,001 | 6/1959 | United Kingdom | 424/213 |

OTHER PUBLICATIONS

The Merck Index–7th Ed.–Merck & Co., Inc. Rahway, N.J., (1960) pp. 236, 631 & 1090.

*Primary Examiner*—Albert T. Meyers
*Assistant Examiner*—D. W. Robinson
*Attorney, Agent, or Firm*—Richard L. Schmalz; Ernest B. Lipscomb, III

[57] ABSTRACT

Disclosed herein are flowable pesticide formulations comprising; 40–60% by weight of the total formulation of a liquid water-insoluble toxicant or mixture of toxicants, 1–25% weight of the total formulation of a hydrocarbon oil from the group consisting essentially of benzene, chlorobenzene and straight chain petroleum aliphatic solvents, 1–10% by weight of the total formulation of an alkali lignin suspending agent, and the remainder being water. When subjected to a higher shear, the lignin suspending agent along with the hydrocarbon oil, liquid toxicant, and water produces a thixotropic formulation with such rheological properties as to prevent or drastically reduce sedimentation and liquid phase separation.

1 Claim, No Drawings

FLOWABLE PESTICIDE FORMULATIONS

CROSS REFERENCE TO RELATED APPLICATIONS

This application is a continuation-in-part of my copending application Ser. No. 404,045, filed Oct. 5, 1973, and now abandoned which was a continuation of my application Ser. No. 181,243, filed Sept. 16, 1971, and now abandoned.

BACKGROUND OF THE INVENTION

1. Field of the Invention

This invention relates to flowable pesticide formulations. More particularly, this invention relates to flowable pesticide formulations in which the pesticide or pesticides are liquid toxicants uniformly dispersed throughout a stable emulsified system for long periods of storage time or can be easily redispersed with mild agitation.

2. The Prior Art

There is a growing demand for pesticide formulations of the flowable type because of the changing methods of application. Some flowables are added via irrigation water, some in the newly developed liquid fertilizer suspension systems and some by conventional means of spraying. Flowable pesticide formulations are usually fluid mixtures of a pesticide or pesticides, suspending agent or agents, and water, with the toxicant concentration generally above 40%. The most important characteristics of a desirable flowable agricultural formulation include; a viscosity low enough to permit the formulation to be pumped, the formulation should disperse readily when it is diluted or added to water, the pesticide should remain suspended without any agitation except the fluid movement which occurs during field transportation, and the diluted formulation should remain suspended until it has been applied in the field.

The desirability of using a flowable pesticide formulation is to overcome many of the disadvantages of using the more conventionally known wettable powder formulations. For example, flowable pesticide formulations are more easily handled, as there is no dusting and little chance of error in mixing the ingredients. An additional disadvantage of a wettable powder formulation is that it is difficult to maintain the wettable powder in a suspension once it is formulated.

One prior art method of preparing flowable pesticide formulations is disclosed in U.S. Pat. No. 2,957,803 to Wood. The Wood formulations are directed to water-insoluble solid organic pesticides that are placed in a flowable suspension by emulsifying the toxicant with a non-oxygen containing fat or oil of animal, mineral or vegetable origin, an emulsifying agent, and sugar or sulfite waste liquor by simultaneously heating and agitating the suspension above 130° F. and cooling to form crystals within the fat globules. Formulations such as those described in the aforementioned patent are limited by the pesticides which may be used and the suspending process for preparing the formulations.

It is, therefore, the general object of this invention to provide a flowable pesticide formulation which maintains suspendibilty over long periods of time or, alternatively, is easily redispersed with mild agitation. Another object of this invention is to provide a flowable pesticide formulation that has a low enough viscosity to be pumped and readily diluted.

Other objects, advantages and features of this invention will be evident from the foregoing detailed description.

SUMMARY OF THE INVENTION

It has been found that alkali lignin suspending agents having a particle size less than 1,000 angstroms, when subjected to high shear along with a liquid toxicant, a hydrocarbon oil selected from the group consisting essentially of benzene, chlorobenzene, toluene and straight chain petroleum aliphatic solvents, and water will produce thixotropic flowable pesticide formulations with such rheological properties so as to provide or drastically reduce sedimentation and liquid phase separation of insoluble pesticides.

A general flowable pesticide-containing formulation contemplated by this invention may be,

| COMPONENT | PERCENT BY WEIGHT, % |
|---|---|
| Liquid Toxicant(s) (Active Ingredient) | 40–60 |
| Hydrocarbon Oil | 1–25 |
| Alkali Lignin Suspending Agent | 1–10 |
| Water | Balance of Composition |

The exact amount of each formulation component is determined by the particular liquid toxicant or toxicants used. The lignin suspending agent is water-insoluble alkali lignins having a particle size less than 1,000 angstroms. The hydrocarbon oil is selected from the group consisting essentially of straight chain aliphatic petroleum solvents, such as Varsol, aromatic hydrocarbon oils, such as benzene, toluene and halogenated hydrocarbon oils, such as chlorobenzene, with the aliphatic solvents being preferred. After the formulation components have been blended together, they are subjected to high shear in order to maintain the formulation in suspension.

DETAILED DESCRIPTION OF THE INVENTION

Maintaining the liquid toxicant in suspension depends upon the particular suspending agent or agents and their relationship to the toxicant in the formulation. It has been found that the alkali lignin and liquid toxiant, when mixed with the hydrocarbon oil and subjected to high shear, form a stable flowable system with the toxicant.

When preparing the flowable formulation, it is essential that the alkali lignin material be maintained in the wet cake state, i.e., precipitated in particles as small as, for example, 150–250 angstroms, but in any event smaller than 1,000 angstroms. The reason the alkali lignin must be used in a wet cake state is that almost any treatment of the lignin particles that have been precipitated, such as heating or drying causes coalescence or agglomeration to larger groups. For example, heating precipitated lignin particles to 180° F. is sufficient to coalesce them into clusters as large as 1,000 angstroms. Drying the lignin may coalesce the particles into even larger sizes, as large as 100 microns. These large dried clusters of lignin are not effective as dispersants in pesticide formulations because they settle rapidly. It is thus necessary when using a water-insoluble lignin suspending agent that the particle size be smaller than 1,000 angstroms to obtain sufficient suspendibility. The advantage of using wet cake lignin is that the surface area of the precipitated lignin is larger than it would be after drying and consequently more is available for adsorption of the pesticides. The total amount of suspending agent used is 1 to 10% by weight of the total flowable formulation. This may be easily accomplished and the desirability to do so depends upon the toxicant used and the properties desired. A process for producing the wet cake small particle size, large surface area alkali lignins is described in U.S. Pat. No. 3,699,093 which issued Oct. 17, 1972, and is incorporated herein by reference.

The next component of the flowable formulations is a hydrocarbon oil. The term "hydrocarbon oil" as used herein is meant to include straight chain aliphatic petroleum hydrocarbon solvents, such as Varsol, aromatic hydrocarbon oils such as benzene, toluene and halogenated hydrocarbon oils, such as chlorobenzene. The aliphatic hydrocarbon oils are preferred, and Varsol is a preferred aliphatic hydrocarbon oil. "Varsol" is the trademark of Humble Oil & Refining Co. for a group of straight chain petroleum solvents. The hydrocarbon oil is used to achieve the desired long term suspendibility as it is believed to act as a bridge between the toxicant and the lignin suspending agents. In some cases, the hydrocarbon oil also aids in lowering the viscosity of the toxicant to improve mixing with lignin suspending agents. The hydrocarbon oil component is used in an amount of from 1 to 25% by weight of the total formulation. It should also be pointed out that the toxicant-suspending agent hydrocarbon oil mixture exhibits some thixotropic properties. An almost ideal thixotropic behavior is obtained in that an extremely small amount of shear is required to make the system fluid. This thixotropic behavior can be altered by varying the lignin suspending agent: hydrocarbon oil ratio, and virtually destroyed by eliminating the hydrocarbon oil.

The active ingredients contemplated for use in the flowable pesticide formulations of this invention include liquid water-insoluble or very slightly water-soluble toxicants employed or adapted to be employed as insecticides, herbicides, fungicides, miticides, nematocides, and rodenticides and include both solid and liquid toxicants. It is also contemplated that a flowable formulation may include more than one toxicant. For example, the formulation may contain both a herbicide and an insecticide. Flowable pesticide formulations of this invention may be prepared from liquid toxicants of the following classes, chlorinated hydrocarbons, organophosphates, carbamates, and substituted phenolics.

A specific example of a liquid chlorinated hydrocarbon is Chloradane (1,2,4,5,6,7,8,8 octachloro-2,3,3a,4,7,7a-hexahydro-4,7-methanoindene).

Specific examples of liquid organophosphates for use in this invention include, Malathion (S-(1,2-dicarbethoxyethyl)-0,0-dimethyl dithiophosphate), and Parathion (O,O-diethyl-O-para-nitrophenyl phosphorothioate).

Specific examples of liquid carbamates suitable for use in this invention are Avadex (S-2,3-Dichloroallyl diisopropyl thiocarbamate), Tillman (S-Propyl butylethyl thiocarbamate), Vegadex (2-chloroallyl diethyl dithiocarbamate) and 2-Sec Butyl phenyl-N-methyl carbamate. A specific example of a liquid substituted phenolic is orthodichlorobenzene. Another toxicant contemplated for use is Lasso (2-chloro-2',6'-diethyl-N-(methoxymethyl acetanilide)). The above list is shown by way of example and is not intended to limit the toxicants useable in this invention.

The liquid toxicant is used in the flowable formulation in an amount of 40% to 60% by weight of the total formulation. Upon subjecting to high shear, these flowable formulations exhibit such rheological properties as to prevent or drastically reduce sedimentation over a long period of time, for instance, 3 months. Further, at the time of application these flowable formulations are readily dilutable.

A general method of making the flowable pesticide formulations of this invention with water-insoluble alkali lignin suspending agents is to precipitate a solution of alkali lignin at low pH, i.e., 2–4, and high shear to form a slurry of 150 – 250 angstrom particles. The alkali lignin slurry may then be filtered to form a wet filter cake of about 30% solids. It is then mixed with the liquid toxicant and hydrocarbon oil in an agitated vessel adding additional water to lower the viscosity of the suspension but maintaining the toxicant concentration at 40% to 60%. Agitation during mixing should be moderate without any areas of high shear turbulence. After mixing, the fomulation is subjected to high shear mixing. By high shear mixing, it is meant that mixing obtained from mixing in a ball mill, wet sand mill or colloid mill, for example.

The following examples will serve to illustrate this invention.

EXAMPLE 1

This example illustrates a flowable pesticide formulation using a large surface area, small particle size, wet filter cake lignin. The flowable formulation comprised the following general formulation, and the various toxicants used along with the results obtained are shown below. The water-soluble lignin was a precipitated lignin and the hydrocarbon oil was Varsol, a straight chain petroleum aliphatic solvent conforming to CS 3-40, the U.S. Department of Commerce commercial standard for Stoddard Solvent.

| Component | Weight Using Chlordane, gms. | Concentration, % |
|---|---|---|
| Toxicant | 66.0 | 50.0 |
| Varsol | 5.0 | 3.8 |
| Wet Cake Lignin | | |
| Lignin | 10.0 | 7.7 |
| Water | 23.0 | 17.3 |
| Additional Water | 28.0 | 21.2 |
| Total | 132.0 | 100.0 |

The wet cake lignin having a particle size of approximately 200 angstroms was mixed with the toxicant and additional water along with the Varsol. After mixing, the formulation was subjected to high shear in a ball mixer and allowed to stand.

| Liquid Toxicant | Suspendability | |
|---|---|---|
| | 1 Week | 3 Months |
| Chlordane | Excellent | Good |
| Vegadex | Excellent | Good |
| Malathion | Good | Good |

The samples which had "excellent" results mean the sample showed undetectable settling. "Good" results only slight settling and redispersion with little agitation.

Each of the formulations of the invention produced suspensions which maintained suspendability over the three-month period.

EXAMPLE 2

To illustrate the importance of the particle size of the alkali lignin, the formulation of Example 1 with Chlordane was prepared using an alkali lignin having a particle size of at least 10,000 angstroms. Upon standing after high shear mixing, the liquid toxicant settled out, thus confirming the advantage obtained with the small particle size lignins.

EXAMPLE 3

To illustrate the suspendability of flowable formulations containing a halogenated hydrocarbon oil, the following composition was formulated and subjected to high shear. To a wet filter cake of precipitated lignin, 10 grams of lignin at about 30% solids, was added 60 grams of Malathion, 7 grams of chlorobenzene, and 30 grams of water. The composition was gently blended in a Homart blender and subjected to high shear. After 3 months of standing, the formulation had separated into two phases but was easily redispersed with mild agitation.

While this invention has been described and illustrated with specific examples and descriptions, it is understood that the invention is not to be limited to the exact details of operation or exact components shown and described herein as obvious modification and equivalents will be apparent to those skilled in the art; and the invention is therefore to be limited only by the scope of the appended claims.

What is claimed is:
1. A flowable pesticide formulation consisting essentially of the following components having been subjected to high shear mixing;
   a. from 40% to 60% by weight of the formulation of a water-insoluble liquid toxicant selected from the group consisting of 1,2,4,5,6,7,8,8 octachloro-2,3,3a,4,7,7a-hexahdyro-4,7-methanoindene; S-(1,2-dicarbethoxyethyl)-O,O-dimethyl dithiophosphate; and 2-chloroallyl diethyl dithiocarbamate,
   b. from 1% to 10% by weight of the formulation of a water-insoluble alkali lignin having a particle size less than 1,000 angstroms,
   c. from 1% to 25% by weight of the formulation of a member of the group consisting of benzene, toluene, chlorobenzene and straight chain petroleum aliphatic hydrocarbon solvents, and
   d. the remainder of the formulation being water.

* * * * *